(12) United States Patent
Rahman

(10) Patent No.: US 10,682,156 B2
(45) Date of Patent: Jun. 16, 2020

(54) ANGLE-GUIDANCE DEVICE AND METHOD FOR CT GUIDED DRAINAGE AND BIOPSY PROCEDURES

(71) Applicant: Akm A. Rahman, Mineola, NY (US)

(72) Inventor: Akm A. Rahman, Mineola, NY (US)

( * ) Notice: Subject to any disclaimer, the term of this patent is extended or adjusted under 35 U.S.C. 154(b) by 1075 days.

(21) Appl. No.: 15/049,932

(22) Filed: Feb. 22, 2016

(65) Prior Publication Data

US 2016/0346004 A1 Dec. 1, 2016

Related U.S. Application Data

(60) Provisional application No. 62/167,441, filed on May 28, 2015.

(51) Int. Cl.
| | | |
|---|---|---|
| A61B 17/34 | (2006.01) |
| A61B 10/02 | (2006.01) |
| A61B 6/12 | (2006.01) |
| A61B 6/00 | (2006.01) |
| A61B 5/06 | (2006.01) |
| A61B 90/11 | (2016.01) |
| A61B 90/00 | (2016.01) |
| A61B 17/00 | (2006.01) |
| A61B 90/13 | (2016.01) |

(52) U.S. Cl.
CPC .......... *A61B 17/3403* (2013.01); *A61B 5/061* (2013.01); *A61B 6/12* (2013.01); *A61B 6/547* (2013.01); *A61B 10/0233* (2013.01); *A61B 90/11* (2016.02); *A61B 90/13* (2016.02); *A61B 2017/00915* (2013.01); *A61B 2017/3407* (2013.01); *A61B 2090/067* (2016.02); *A61B 2090/395* (2016.02); *A61B 2562/0219* (2013.01)

(58) Field of Classification Search
None
See application file for complete search history.

(56) References Cited

U.S. PATENT DOCUMENTS

| | | | |
|---|---|---|---|
| 4,170,993 A * | 10/1979 | Alvarez | A61M 25/0637 |
| | | | 128/DIG. 26 |
| 4,469,106 A | 9/1984 | Harui | |
| 4,733,661 A * | 3/1988 | Palestrant | A61B 17/3403 |
| | | | 128/DIG. 26 |
| 4,899,756 A | 2/1990 | Sonek | |
| 4,930,525 A | 6/1990 | Palestrant | |

(Continued)

*Primary Examiner* — Katherine L Fernandez
(74) *Attorney, Agent, or Firm* — Michael D. Einsenberg

(57) ABSTRACT

An angle guidance device includes a base, which can be flexible and self-adhesive; a connector piece, including a rotatable connection, which is tiltable to a left or right side, and right and left connector plates, each including center and protractor cutouts; and a guidance piece, including an insert or protractor piece, and v-shaped needle guide, such that the v-shaped needle guide can be adjusted to a predetermined device inclination angle relative to the base. Optionally included are longitudinal and lateral level components, a bullseye level, a laser pointer, a screen, and an angle-guidance control unit, including a processor, a non-transitory memory, an input/output, a CT controller, an angle sensor, an angle viewer, a 3-axis accelerometer, and a data bus. Also disclosed is an angle-guidance method, including obtaining CT images, measuring angle and depth, setting biopsy angle, marking entry point, positioning angle-guidance device, marking position, inserting procedure needle.

16 Claims, 10 Drawing Sheets

Angle Guidance Device

(56) References Cited

U.S. PATENT DOCUMENTS

| | | | | |
|---|---|---|---|---|
| 4,966,589 A | * | 10/1990 | Kaufman | A61M 25/02 |
| | | | | 128/DIG. 26 |
| 5,053,042 A | | 10/1991 | Bidwell | |
| 5,078,142 A | | 1/1992 | Siczek et al. | |
| 5,102,391 A | | 4/1992 | Palestrant | |
| 5,320,111 A | | 6/1994 | Livingston | |
| 5,682,892 A | | 11/1997 | Selder | |
| 5,957,933 A | * | 9/1999 | Yanof | A61B 90/11 |
| | | | | 606/129 |
| 5,984,930 A | | 11/1999 | Maciunas et al. | |
| 6,203,499 B1 | | 3/2001 | Imling et al. | |
| 6,249,713 B1 | | 6/2001 | Geiger et al. | |
| 6,612,990 B1 | | 9/2003 | Pruter | |
| 7,351,205 B2 | | 4/2008 | Szczech et al. | |
| 7,635,336 B1 | | 12/2009 | Pruter | |
| 7,708,751 B2 | | 5/2010 | Hughes et al. | |
| 7,711,407 B2 | | 5/2010 | Hughes et al. | |
| 8,162,852 B2 | | 4/2012 | Norris | |
| 9,044,216 B2 | | 6/2015 | O'Laughlin | |
| 2005/0080333 A1 | * | 4/2005 | Piron | A61B 8/0825 |
| | | | | 600/417 |
| 2005/0267373 A1 | * | 12/2005 | Lee | A61B 8/0833 |
| | | | | 600/471 |
| 2006/0229641 A1 | | 10/2006 | Gupta et al. | |
| 2013/0218024 A1 | * | 8/2013 | Boctor | A61B 34/20 |
| | | | | 600/476 |
| 2015/0238266 A1 | | 8/2015 | Fujimoto et al. | |

* cited by examiner

Angle Guidance Device

Angle-Guidance Biopsy System

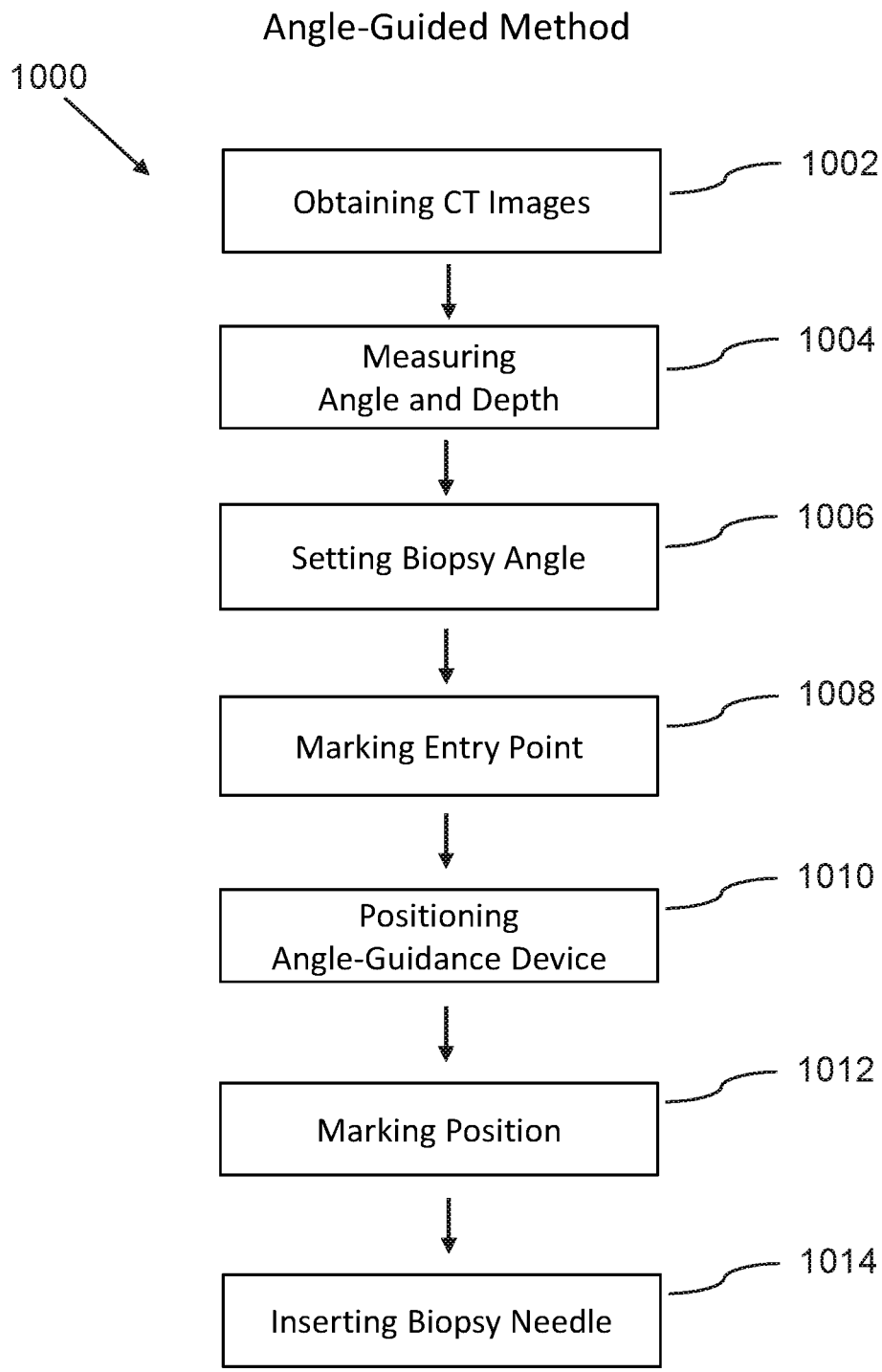

ANGLE-GUIDANCE DEVICE AND METHOD FOR CT GUIDED DRAINAGE AND BIOPSY PROCEDURES

CROSS-REFERENCE TO RELATED APPLICATIONS

This application claims the benefit of U.S. Provisional Application No. 62/167,441, filed May 28, 2015.

FIELD OF THE INVENTION

The present invention relates generally to the field of CT guided needle drainage and biopsy procedures, and more particularly to methods and systems for directing the angle of a needle during such procedures.

BACKGROUND OF THE INVENTION

CT scanners are widely used for cross-sectional imaging of the body. CT scanners which are presently available are capable of measuring a proposed trajectory for a biopsy needle or drainage catheter including the estimated depth and angle.

Most radiologists use a visual approximation of the optimal angle of the biopsy catheter/needle during the procedure. Current CT scanners provide laser guidance to choose the entry point on the skin. However, that does not guide the radiologist to choose the correct angle for the biopsy. Vertical trajectory at a 90-degree angle does not always provide an accurate access method. There may also be organs such as bowel, liver, heart, or kidney between the access point and the target. Thus, the needle needs to be manipulated by the radiologist to obtain access to the target.

Most radiologists perform CT-guided procedures by choosing the entry point on the skin and placing grid lines on the skin. CT lasers and grids thus help to identify the entry point. Then, the radiologist advances the needle slowly at an approximate estimation of the desired angle. Multiple individual small volume acquisitions of CT images are obtained throughout the procedure to determine the actual position of the needle or catheter and altering its trajectory as needed. Normally, radiologist may need a minimum of 3 to 4 CT acquisitions to obtain a tissue sample from the target This trial-and-error technique has major disadvantages. Firstly, it usually requires the patient to remain in a fixed position, lying supine or prone for a relatively long period of time, which most patients find uncomfortable. Secondly, the increased radiation dose from the multiple CT image acquisitions is potentially harmful to the patient. Additionally, in practices where CT access is limited, a relatively lengthy procedure will delay other CT examinations.

As such, considering the foregoing, it may be appreciated that there continues to be a need for novel and improved devices and methods for guiding a needle during CT guided biopsy and drainage procedures.

SUMMARY OF THE INVENTION

The foregoing needs are met, to a great extent, by the present invention, wherein in aspects of this invention, enhancements are provided to the existing model of guiding a needle during CT guided biopsy and drainage procedures.

In an aspect, an angle-guidance device includes a base; and a guidance piece, which is rotatably connected to an upper side of the base, the guidance piece including an insert piece; and a needle guide, which is connected to an upper part of the insert piece; such that the needle guide can be inclined up or down, at a device inclination angle of the needle guide relative to the base; whereby a biopsy needle is guided by the v-shaped needle guide, such that the biopsy needle slides along the bottom inside of the v-shaped needle guide, such that the biopsy needle is inserted in a patient with a predetermined device inclination angle.

In a related aspect, the insert piece can include a protractor piece, which includes angle markings.

In another related aspect, the needle guide can be v-shaped.

In yet a related aspect, the guidance piece can be configured to be tilted to a left or right side.

In a further related aspect, the angle-guidance device can further include a connector piece, which is connected to an upper side of the base; such that the connector piece is configured to be tiltable to a left or right side angle.

In a related aspect, the angle-guidance device can further include a laser pointer, which is mounted in a front end of the v-shaped needle guide.

In a related aspect, the angle-guidance device can further include a screen and an angle-guidance control unit, including:
  a) a processor;
  b) a non-transitory memory;
  c) an input/output;
  d) an angle sensor, which is configured to measure the device inclination angle; and
  e) an angle viewer, which is configured to present the device inclination angle on the screen via the input/output; all connected via
  f) A data bus.

In an aspect, an angle-guidance method for CT guided drainage and biopsy procedures, can include:
  a) TBD There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 10 is a flowchart illustrating steps that may be followed, in accordance with one embodiment of an angle-guided method or process for biopsy and drainage.

DETAILED DESCRIPTION

Figure 1:
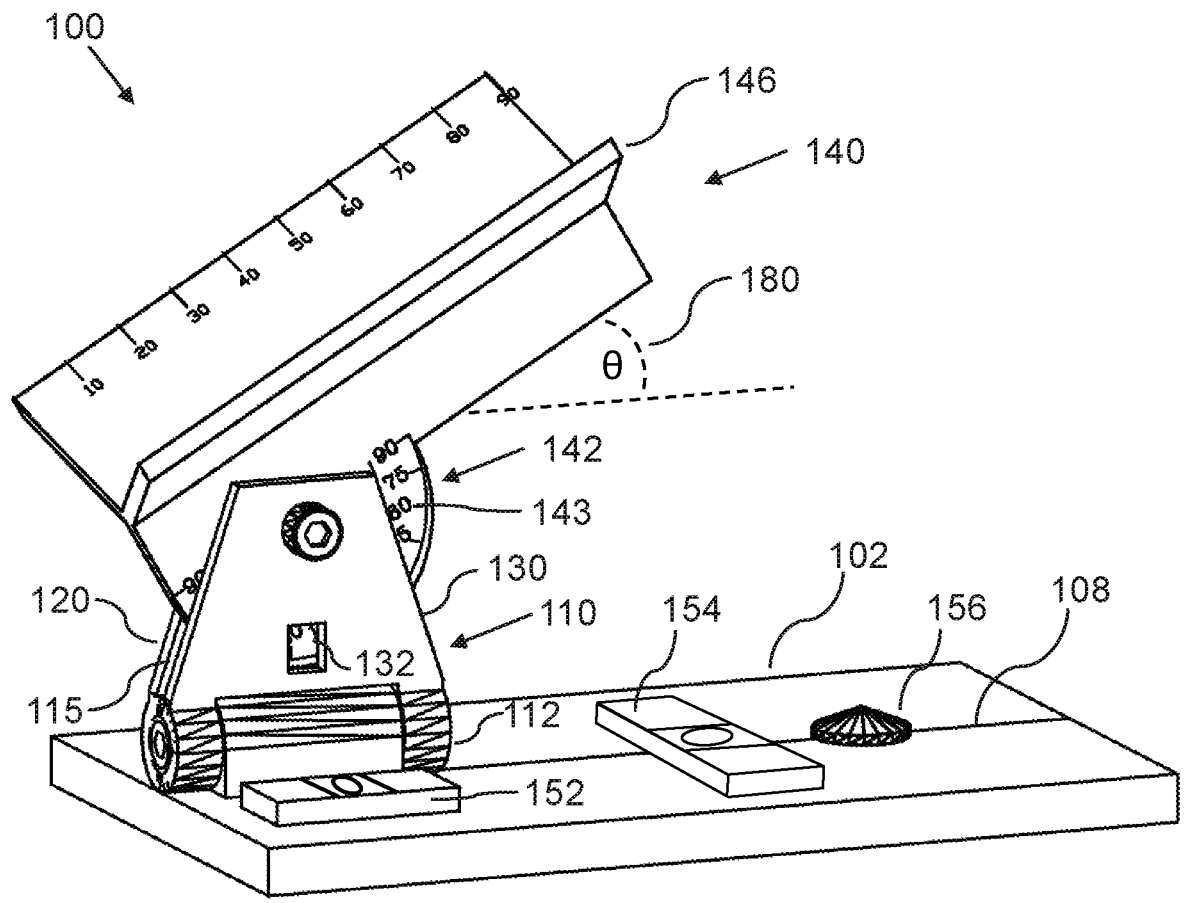
FIG. 1 is a perspective view of an angle-guidance device, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of an angle-guidance device 100 with reference to FIG. 1, in such manner that like reference numerals refer to like components throughout; a convention that we shall employ for the remainder of this specification.

In various embodiments, the angle-guidance device 100 is designed for use in performing CT-guided biopsy and drainage procedures. The angle-guidance device 100 can be used for biopsy of solid organs of the abdomen and pelvis, i.e., liver, kidney, spleen, and bone, as well as for drainage of abscesses. The angle-guidance device 100 can also be used for injection of the facet joints of the vertebrae, hip joints and other neuro-interventional procedures.

In related embodiments, the angle-guidance device 100 can help radiologists to find the accurate angle and level for a biopsy gun, biopsy needle, or drainage catheter. A v-shaped piece or catheter/biopsy needle support piece can be easily adjusted to an accurate angle between a biopsy needle/catheter and a skin surface of a patient. The required angle for the procedure will be determined from a CT scan performed at the start of the procedure. After measuring the best or optimum angle of the biopsy catheter/needle for the procedure from the CT control room computer screen monitor, the v-shaped piece can be adjusted to that angle.

In an embodiment, as shown in FIG. 1, an angle-guidance device 100 can include:

a) a base 102;
b) a connector piece 110, which is connected to an upper side of the base 102, such that it is configured to be tiltable to a left or right side; and
c) a guidance piece 140, which is rotatably connected to an upper side of the base 102, such that the guidance piece can be tilted up or down, at a device inclination angle 180 of the v-shaped needle guide 146 relative to the base 102;
such that the guidance piece 140 can further include:
   i. an insert piece 142, which can include a protractor piece 142, which further includes angle markings 143
   ii. a v-shaped needle guide 146, which is connected to an upper part of the insert/protractor piece 142;
such that the v-shaped needle guide 146 can be adjusted to a predetermined device inclination angle 180 of the v-shaped needle guide 146 relative to the base 102;
whereby a biopsy needle can be guided by the v-shaped needle guide 146, such that the biopsy needle slides in the bottom inside of the v-shaped needle guide 146, such that the biopsy needle can be inserted in a patient with the predetermined device inclination angle 180.

Figure 4:
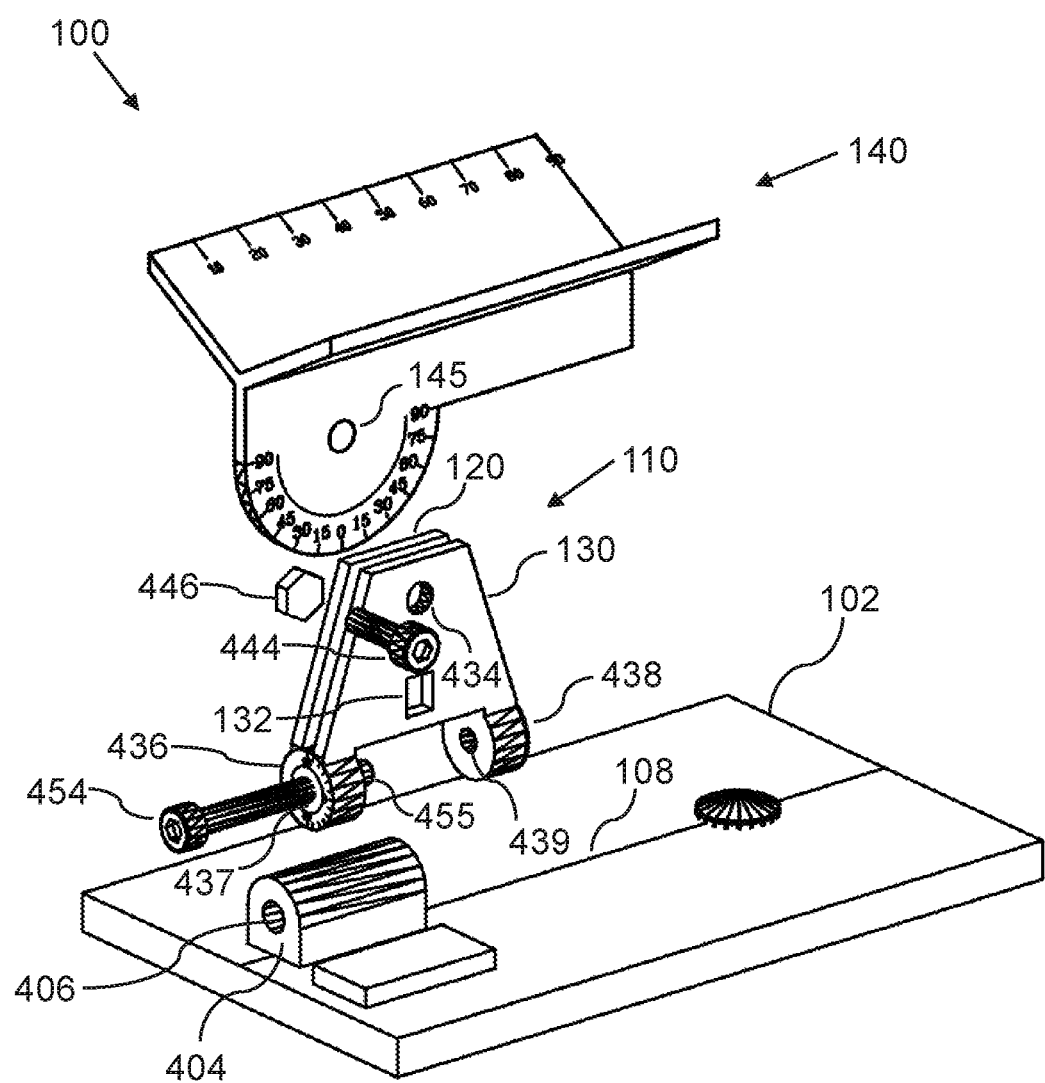
FIG. 4 is a left side exploded perspective view of an angle-guidance device, according to an embodiment of the invention.
Figure 5:
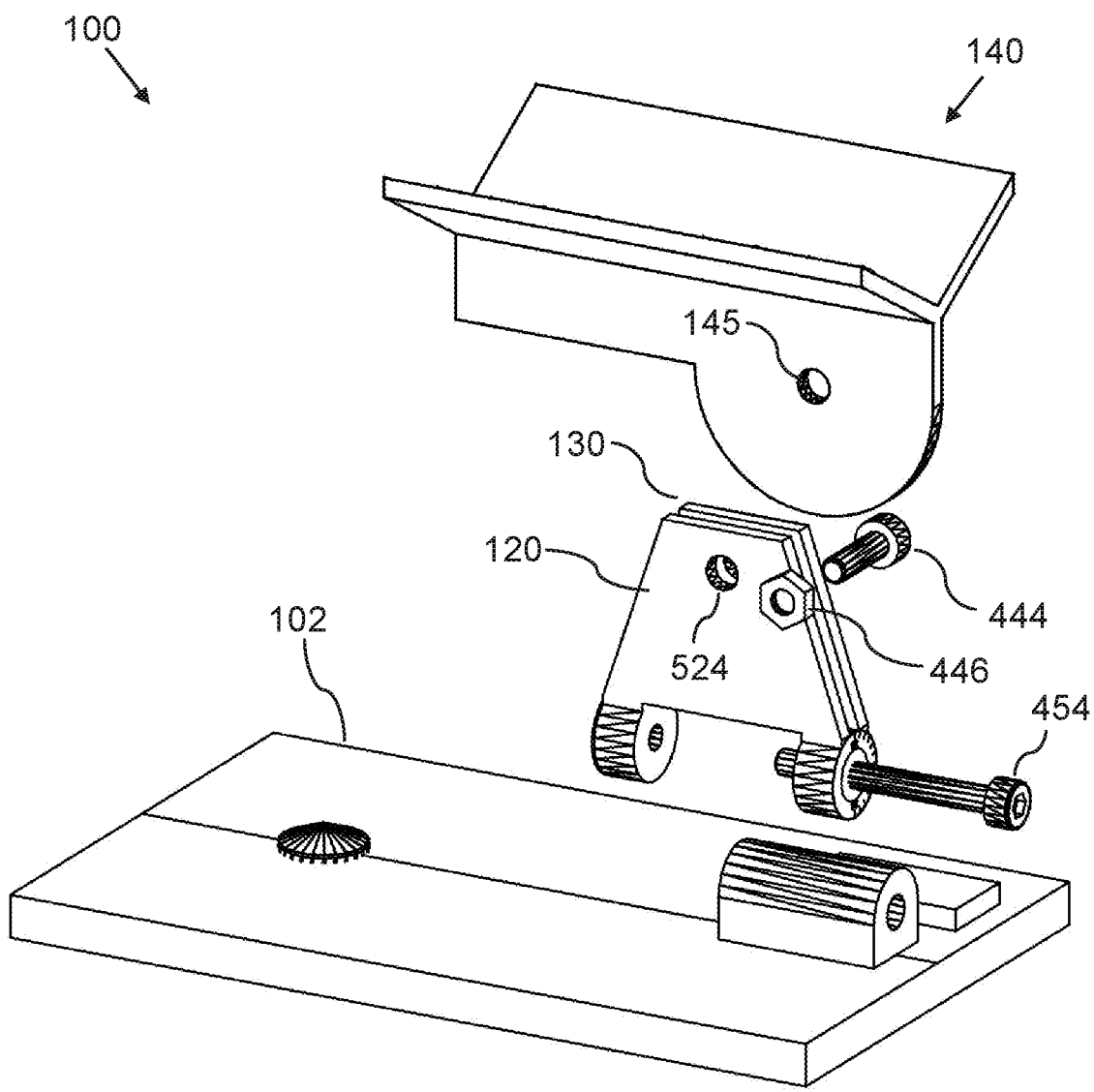
FIG. 5 is a right side exploded perspective view of an angle-guidance device, according to an embodiment of the invention.

In a related embodiment, the connector piece 110 can further include:

a) a rotatable connection 112, which can be a rotatable cylinder 112, which is rotatably connected to an upper side of the mounting base, such that the connector piece can be tilted to a right or left side;
b) a right connector plate 120, which is connected to an upper part of the rotatable cylinder 112, such that the right connector plate 120 protrudes vertically when the rotatable cylinder is in a non-rotated position, wherein the right connector plate 120 can further include:
   i. a right protractor cutout; and
   ii. a right pivotal aperture 524, as shown in FIG. 5;
c) a left connector plate 130, which is connected to an upper part of the rotatable cylinder 112, such that the left connector plate 130 protrudes vertically when the rotatable cylinder is in a non-rotated position, wherein the left connector plate 130 can further include:
   iii. a left protractor cutout 132; and
   iv. a left pivotal aperture 434, as shown in FIG. 4;
wherein the right and left connector plates 120 130 are parallel and mounted side by side, such that there is plate gap 115 between the plates 120 130, such that the plate gap is configured to accept the insert/protractor piece 142, such that the insert/protractor piece 142 is rotatably connected between the right and left pivotal apertures 524 434, such that angle markings 143 are visible through the right and left protractor cutout 132 (right protractor cutout not shown), such that the angle markings are configured to indicate a device inclination angle 180.

In a further related embodiment, the angle guidance device 100 can further include:

a) a longitudinal level component 152, which is configured to show if the angle-guidance device 100 is level in the longitudinal direction, and further indicate a longitudinal deviation from level. The longitudinal level component 152 can be mounted to an upper surface of the base 102; and
b) a lateral level component 154, which is configured to show if the angle-guidance device 100 is level in the lateral direction, and further indicate a cross-wise deviation from level. The lateral level component 154 can be mounted to an upper surface of the base 102; and In a yet further related embodiment, the longitudinal and side-to-side level components 152 154 can be bubble levels, also referred to as spirit levels.

In another related embodiment, the angle guidance device 100 can further include a bullseye level 156, also referred to as a circular level 156, which indicates both longitudinal and lateral level, and thereby functions as an alternative to separate longitudinal and side-to-side level components 152 154.

Figure 2:
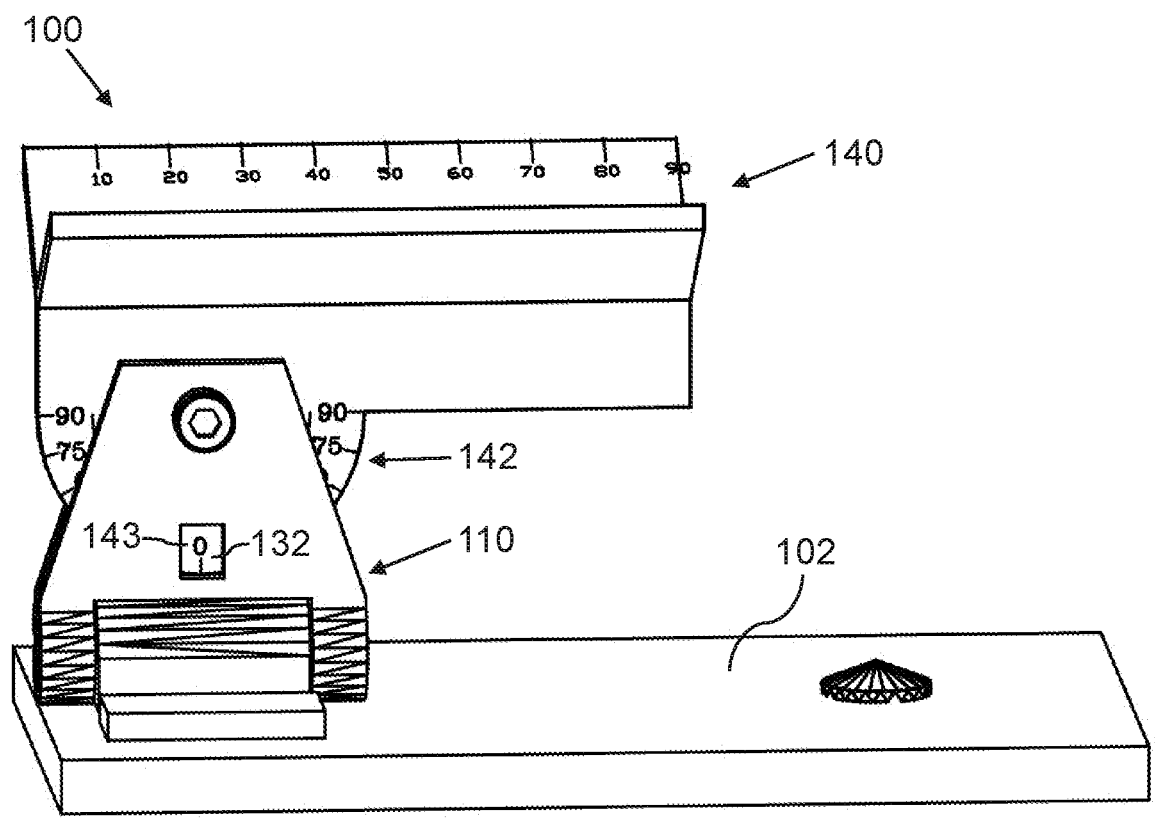
FIG. 2 is a side perspective view of an angle-guidance device, according to an embodiment of the invention.

In a related embodiment, FIG. 2 shows a side perspective view of an angle-guidance device 100 in a non-inclined position, such that the device inclination angle 180 is indicated to be 0 degrees, as indicated by the angle marking 143 in the left protractor cutout 132.

Figure 3:
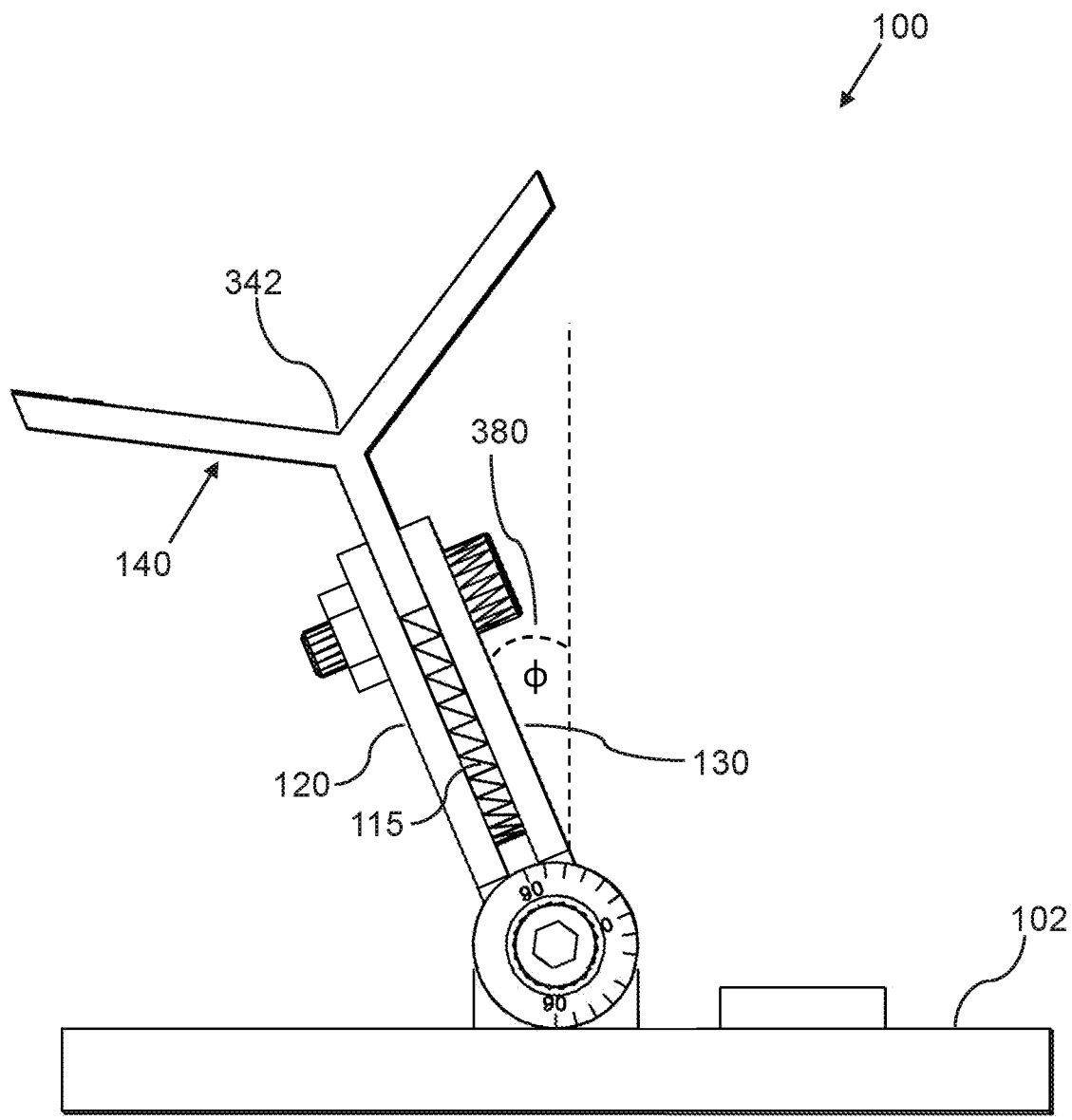
FIG. 3 is a front view of an angle-guidance device, according to an embodiment of the invention.

In a related embodiment, FIG. 3 shows a front view of an angle-guidance device 100, which is tilted to a right side at a side angle 380 of approximately 30 degrees, further showing the bottom inside 342 of the v-shaped needle guide 146.

In a related embodiment, FIGS. 4 and 5 show respectively left and right exploded perspective views of components of an angle-guidance device 100, showing:
 a) the left and right pivotal apertures 434 524;
 b) the left protractor cutouts 132, such that the right side of the protractor in this embodiment does not have a right protractor cutout.

In a related embodiment, the angle-guidance device 100 can further include:
 a) a threaded protractor bolt 444;
 b) a protractor nut 446;
 c) a threaded connector bolt 454, which can be threaded on an outer end 455;
 d) the connector piece 110, further including
  i. a front connector flange 436, with a front flange aperture 437; and
  ii. a rear connector flange 438, with a threaded rear flange aperture 439;
 e) a center connector 404, with a center aperture 406, such that the center connector is mounted on an upper side of the base, for example in a front center position of the base 102; such that the front and rear connector flanges 436 438 are configured to slide on respectively a front and rear of the center connector 404, such that the center connector is mounted in between the front and rear connector flanges 436 438, such that the connector bolt 454 is inserted through the front flange aperture 437 and the center aperture 406, and screwed into the threaded rear flange aperture 439, such that the connector piece is rotatably connected to the center connector;

such that the right and left connector plates 120 130 are parallel and mounted side by side, such that there is plate gap 115 between the plates 120 130, such that the plate gap 115 is configured to accept the protractor piece 142, such that the threaded protractor bolt 444 is inserted through right and left connector plate pivotal apertures 524 434 and a protractor aperture 145 of the protractor piece 142, such that the protractor bolt 444 is secured in place with the protractor nut 446 screwed on the end of the protractor bolt 444, such that the protractor piece 142 is rotatably connected between the right and left pivotal aperture 524 434.

Figure 6:
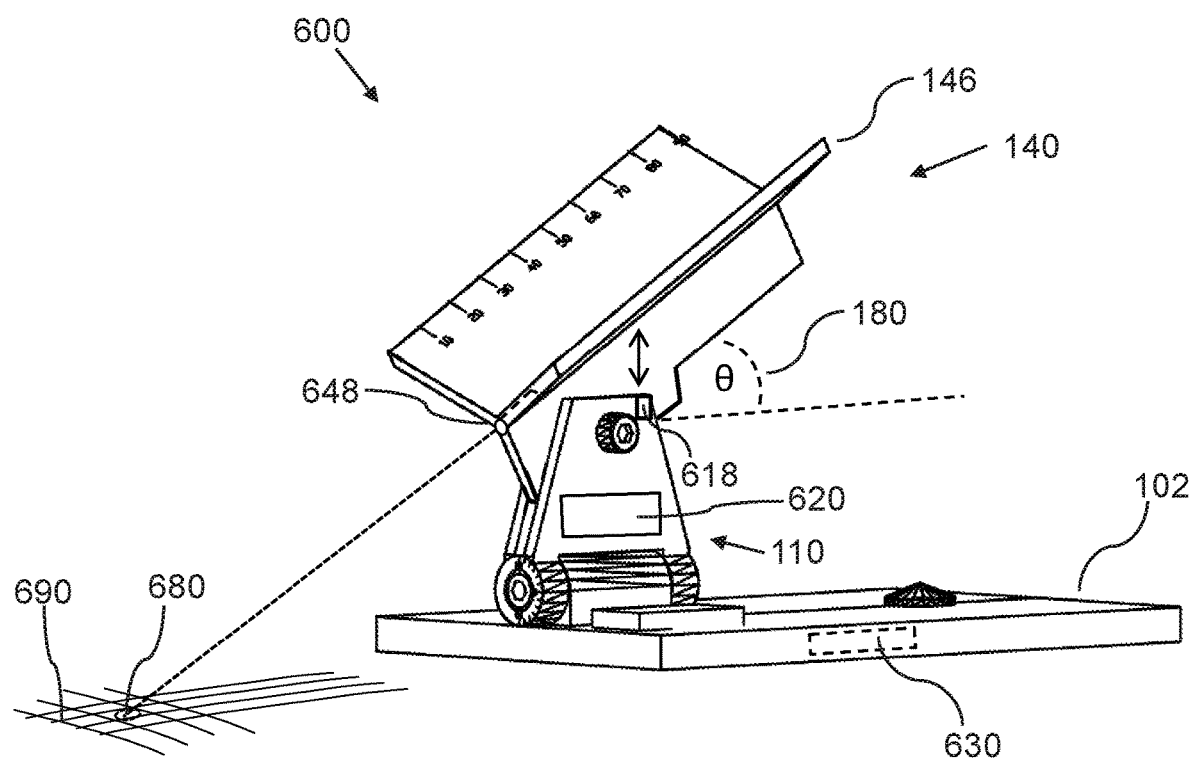
FIG. 6 is a perspective view of an angle-guidance device, according to an embodiment of the invention.
Figure 7:
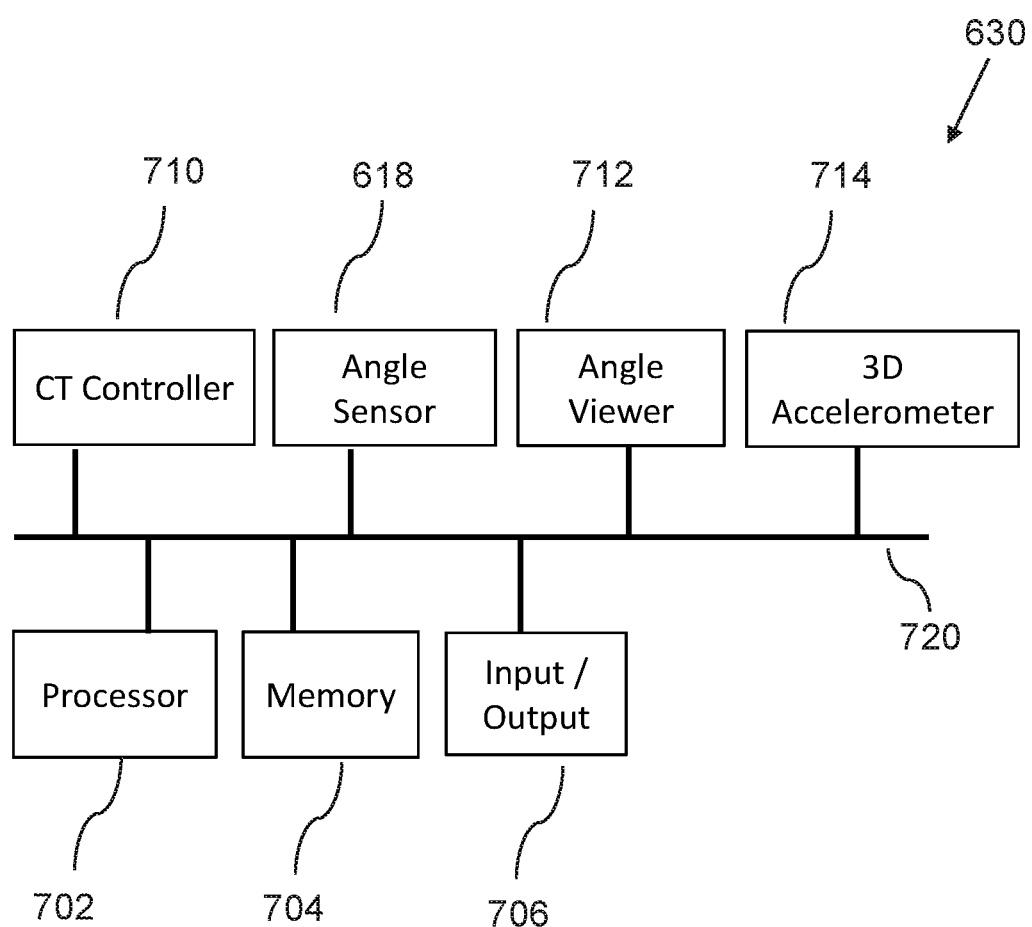
FIG. 7 is a schematic diagram illustrating an angel-guidance control unit, according to an embodiment of the invention.

In a related embodiment, as shown in FIG. 6, an angle-guidance device 600 can further include:

a) a laser pointer 648, which is mounted in a front end of the v-shaped needle guide 146, such that the laser pointer 648 is configured to point in a direction of the v-shaped needle guide 146, thereby indicating the targeted point 680 on the surface of a patient;
 b) an angle sensor 618, which is configured to measure a device inclination angle 180 of the guidance piece 140 relative to the base 102. The angle sensor 618 can for example be a laser sensor which measures a distance to the guidance piece 140, and converts this measurement to an angle, or it can be a rotational sensor;
 c) A screen 620, which is configured to display the device inclination angle 180. The screen 620 can for example, as shown, be attached to the connector piece 110, or alternatively it can be attached on another area of the angle-guidance device 600, such as the base 102;
 d) An angle-guidance control unit 630, which is configured to control electronic functions of the angle-guidance device 100. The angle-guidance control unit 630 can for example, as shown, be built into the base 102, or alternatively the angle-guidance control unit 630 can be attached to another part of the angle-guidance device 600, such as the connector piece 110.

In a related embodiment, FIG. 6 also shows a CT grid 690 that has been positioned on the body of a patient.

In a related embodiment, the angle-guidance control unit 630 can comprise:
 a) A processor 702;
 b) A non-transitory memory 704;
 c) An input/output 706;
 d) A CT controller 710, which is configured to communicate with a CT scanner;
 e) The angle sensor 618;
 f) An angle viewer 712, which is configured to present the device inclination angle 180 on the screen 620, via the input/output 706; and
 g) A 3-axis accelerometer 714, which is configured to measure 3-axis rotation and movement; all connected via
 h) A data bus 720.

Figure 8:
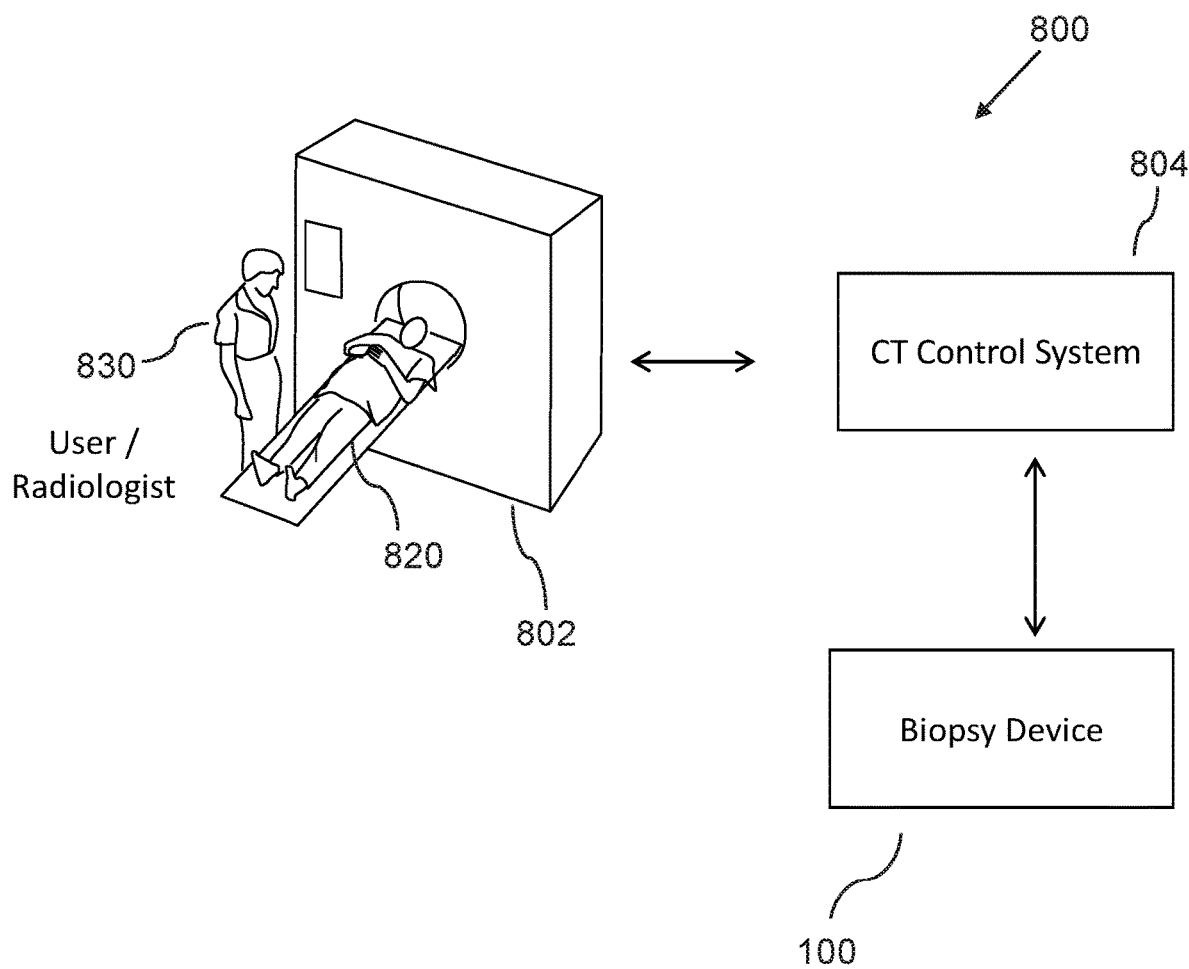
FIG. 8 is a schematic diagram illustrating an angel-guidance system, according to an embodiment of the invention.

In an embodiment, FIG. 8 illustrates a schematic diagram of an angle-guidance system 800, including
 a. ACT scanner 802;
 b. A CT control system 804, which further includes a CT control screen, wherein the CT control system 804 is configured to control functions of the CT scanner 802;
 c. An angle-guidance device 100 600, which optionally can communicate with the CT control system 804;
 whereby a patient 820 can be treated by a medical practitioner 830.

Figure 9:
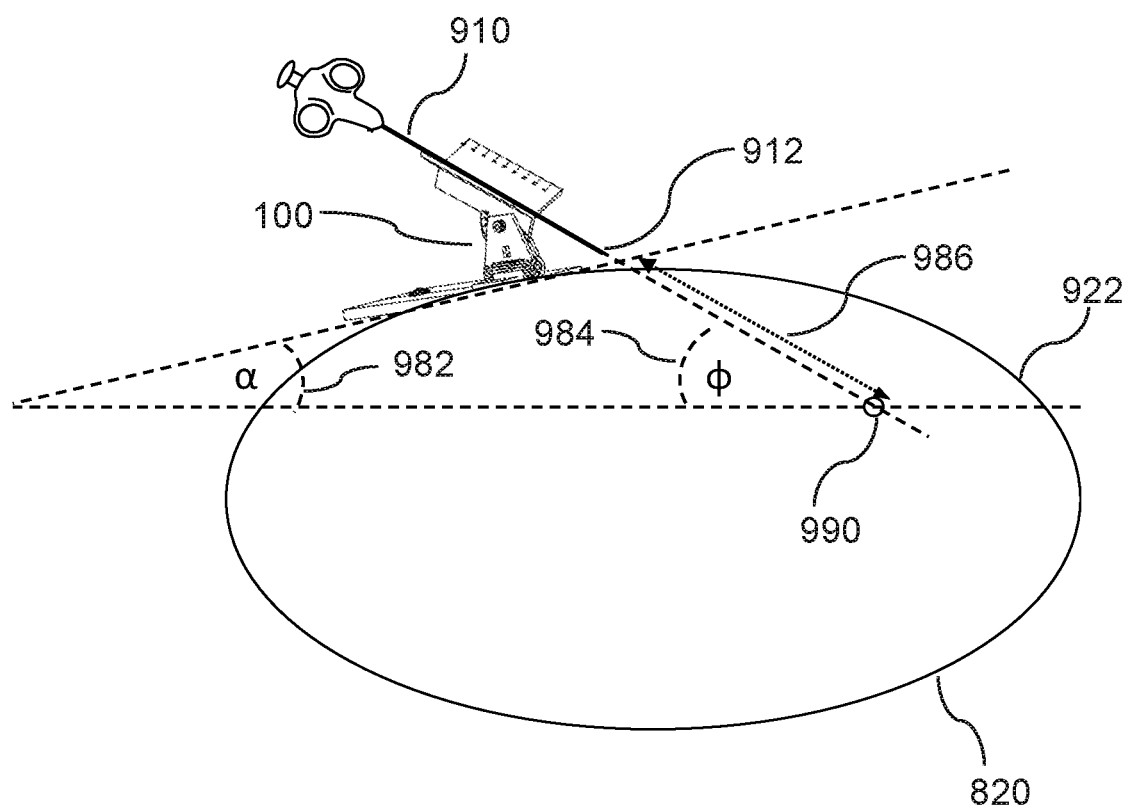
FIG. 9 is a schematic diagram illustrating an angel-guidance control unit in use on a patient, according to an embodiment of the invention.

In an embodiment, FIG. 9 illustrates a cross-sectional view a patient 820 with an angle-guidance device 100 600 positioned on the skin surface 922 in a direction that is parallel to the cross-sectional plane;
wherein the direction of the v-shaped needle guide 146 points in a direction of a targeted area 990, such that a biopsy needle 910 inserted in the shaped needle guide 146 points in the direction of the targeted area 990;
such that the device inclination angle 180 equals the sum of the horizontal inclination angle 982 and the relative inclination angle 984.

In related embodiments, the base 102 can be flexible, such that is can adapt to the surface of a patient's 820 skin, by curving or bending the base. Additionally, the base 102 can have a sticky undersurface, such as an adhesive pad made in a solid gel or rubber material, such as used for self-adhesive pads used for a resuscitation or electrical stimulation, including materials commonly used for cardiac defibrillator pads.

In related embodiments, the base 102 can be made from a plastic, rubber, or solid gel material, and can be transparent, translucent, or opaque.

In a related embodiment, as shown in FIG. 1, the base 102 can further include a centerline 108, which is a printed and/or cut/indented line along a center of the base 102, parallel to the elongated direction of the guidance piece 140, such that the centerline 108 can be used to orient the angle-guidance device 100 600 along grid lines indicated on the skin of a patient 820, such as grid lines drawn by a medical practitioner 830 or indicated by CT laser gridlines.

In related embodiments, parts of the angle-guidance device 100 600, including the guidance piece 140 and the connector piece 110 can be made in a plastic material, such as polypropylene, acrylonitrile butadiene styrene and polyvinyl chloride.

In related embodiments, parts of the angle-guidance device 100 600, including the guidance piece 140 and the connector piece 110 can be made in a transparent shatter-resistant plastic material, such as polycarbonate and polymethyl methacrylate.

In an embodiment, as illustrated in FIG. 10, with further reference to the system overview shown in FIG. 8 and the cross-sectional view shown in FIG. 9, an angle-guidance method 1000 for CT guided drainage and biopsy procedures, can include:

a) Obtaining CT images 1002, wherein a user/radiologist 830 places a grid 690 on a body of a patient 820 and obtains a preliminary small volume acquisition of CT images of a part of the body of the patient, wherein the part contains a tumor/abscess/targeted area;

b) Measuring angle and depth 1004, wherein the user 830 measures the targeted device inclination angle 180 and the targeted depth 986 from an entry point on the skin surface 922 to the biopsy/drainage target location (target lesion) in the body;

c) Setting biopsy angle 1006, wherein the user 830 sets the angle-guidance device 100 to the targeted device inclination angle 180, by rotating the v-shaped needle guide 146;

d) Marking entry point 1008, wherein the user 830 marks the entry point on the skin surface 922 with a "+" sign and extends a lateral line, which is perpendicular to an elongated direction of the body of the patient, such that the lateral line extends on both right and left sides of the entry point, by reference to the grid.

e) Sterilizing, wherein the user 830 sterilizes the skin surface and applies local anesthesia, while maintaining sterile technique throughout the procedure;

f) Positioning device 1010, wherein the user 830 aligns a laser tip of the angle-guidance device 100 with the lateral line and advances the laser tip to the center/intersection of the "+" sign, such that a centerline 108 of the angle-guidance device 100 follows the lateral line;

g) Marking device position 1012, wherein the user 830 marks the location of the angle-guidance device 100 on the skin by marking the front and back position of the angle-guidance device 100 on the skin;

h) Inserting procedure needle 1014, wherein the procedure needle 910 can be a biopsy needle, a drainage needle, or other surgical needle, wherein the user places the procedure needle on the v-shaped needle guide 146 of the angle-guidance device 100, and gradually advances the procedure needle to the target location; wherein inserting procedure needle 1014 can further include:

a. Advancing the procedure needle 910 along the bottom inside 342 of the v-shaped needle guide 146 towards the laser/entry point on the skin;

b. Advancing the procedure needle 910 tip 912 to half of the total depth to the target location/lesion;

c. Obtaining a small volume CT acquisition of the target location;

d. Optionally, rotating the connector piece right or left based on image findings, if any adjustments of the needle angle are required; and e. Advancing the procedure needle to the full depth and obtaining a biopsy, thereby completing the procedure.

FIGS. 6, 7, 8, and 10 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 6, 7, 8, and 10 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

It shall be understood that the above-mentioned components of the angle-guidance control unit 630 are to be interpreted in the most general manner.

For example, the processors 702, can include a single physical microprocessor or microcontroller, a cluster of processors, a datacenter or a cluster of datacenters, a computing cloud service, and the like.

In a further example, the non-transitory memory 704 can include various forms of non-transitory storage media, including random access memory and other forms of dynamic storage, and hard disks, hard disk clusters, cloud storage services, and other forms of long-term storage. Similarly, the input/output 706 can include a plurality of well-known input/output devices, such as screens, keyboards, pointing devices, motion trackers, communication ports, and so forth.

Furthermore, it shall be understood that the angle-guidance control unit 630 can include a number of other components that are well known in the art of general computer devices, and therefore shall not be further described herein. This can include system access to common functions and hardware, such as for example via operating system layers such as Windows, Linux, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the angle-guidance control unit 630 communicates with the CT control system 804 over a network, which can include the general Internet, a Wide Area Network or a Local Area Network, or another form of communication network, transmitted on wired or wireless connections. Wireless networks can for example include Ethernet, Wi-Fi, Bluetooth, ZigBee, and NFC. The communication can be transferred via a secure, encrypted communication protocol.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like.

Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the . . . device, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. An angle-guidance device, comprising:
 a) a base; and
 b) a guidance piece, which is rotatably connected to an upper side of the base, the guidance piece comprising:
  an insert piece, rotatably connected to the base with respect to a longitudinal rotation axis; and
  a v-shaped needle guide, which is connected to an upper part of the insert piece, the v-shaped needle guide comprising two plates meeting at an axis located at the upper part of the insert piece to form a v-shape centered above the insert piece;
 wherein the v-shaped needle guide is configured to be inclined up or down, at a device inclination angle of the v-shaped needle guide relative to the base;
 whereby a biopsy needle is adapted to be guided by the v-shaped needle guide, such that the biopsy needle slides in the bottom inside of the v-shaped needle guide, such that the biopsy needle is adapted to be inserted in a patient with a predetermined device inclination angle;
 wherein:
 wherein the guidance piece is configured to be tilted by being rotatable about a lateral rotation axis which is perpendicular to the longitudinal rotation axis;
 the angle-guidance device further comprises a connector piece, which is connected to an upper side of the base, such that the connector piece is configured to be tiltable by being rotatable about the lateral horizontal rotation axis;
 the connector piece further comprises:
  a rotatable connection, which is rotatably connected to an upper side of the base, such that the connector piece can be rotated about the lateral horizontal rotation axis;
  a right connector plate, which is connected to an upper part of the rotatable connection, such that the right connector plate protrudes vertically when the rotatable connection is in a non-related position, wherein the right connector plate further comprises a right pivotal aperture;
  a left connector plate, which is connected to an upper art of the rotatable connection, such that the left connector plate protrudes vertically when the rotatable connection is in the non-rotated position, wherein the left connector plate further comprises a left pivotal aperture;

the right and left connector plates are parallel and mounted side by side, such that there is a plate gap between the right and let connector plates, such that the plate gap is configured to accept the insert piece, such that the insert piece is rotatably connected between the right and left pivotal apertures, such that anile markings are configured to indicate the device inclination angle.

2. The angle-guidance device of claim 1, wherein the insert piece includes a protractor piece, which includes the angle markings.

3. The angle-guidance device of claim 1, wherein the rotatable connection is a rotatable cylinder.

4. The angle-guidance device of claim 1, wherein the insert piece includes a protractor piece, which includes the angle markings; and wherein at least one of the right and left connector plates further comprises:
   a protractor cutout,
   which is configured such that the angle markings are visible through the protractor cutout.

5. The angle-guidance device of claim 1, wherein the base is flexible.

6. The angle-guidance device of claim 1, wherein the base is self-adhesive.

7. The angle-guidance device of claim 1, further comprising:
   a longitudinal level component, which is configured to show a level indication in a longitudinal direction.

8. The angle-guidance device of claim 1, further comprising:
   a lateral level component, which is configured to show a level indication in a lateral direction.

9. The angle-guidance device of claim 1, wherein the angle-guidance device further comprises:
   a laser pointer, which is mounted in a front end of the v-shaped needle guide, such that the laser pointer is configured to point in a direction of the v-shaped needle guide, thereby indicating a targeted point on a surface of a patient.

10. The angle-guidance device of claim 1, wherein the angle-guidance device further comprises a screen and an angle-guidance control unit, comprising:
   a) a processor,
   b) a non-transitory memory;
   c) an input/output;
   d) an angle sensor, which is configured to measure the device inclination angle; and
   e) an angle viewer, which is configured to present the device inclination angle on the screen via the input/output; all connected via
   f) a data bus.

11. The angle-guidance device of claim 10, wherein the angle-guidance control unit further comprises:
   a CT controller, which is configured to communicate with a CT scanner.

12. The angle-guidance device of claim 10, wherein the angle-guidance control unit further comprises:
   a 3-axis accelerometer, which is configured to measure 3-axis rotation and movement of the angle guidance device.

13. An angle-guidance device, comprising:
   a) a base; and
   b) a guidance piece, which is rotatably connected to an upper side of the base, the guidance piece comprising:
     an insert piece; and
     a needle guide, which is connected to an upper part of the insert piece;
   wherein the needle guide is configured to be inclined up or down, at a device inclination angle of the needle guide relative to the base,
   whereby a biopsy needle is adapted to be guided by the needle guide, such that the biopsy needle slides in the bottom inside of the needle guide, such that the biopsy needle is adapted to be inserted in a patient with a predetermined device inclination angle;
   wherein:
   the guidance piece is configured to be tilted by being rotatable about a horizontal rotation axis;
   the angle-guidance device of further comprises:
     a connector piece, which is connected to an upper side of the base, such that the connector piece is configured to be tiltable by being rotatable about the horizontal rotation axis;
   the connector piece further comprises:
     a rotatable connection, which is rotatably connected to an upper side of the base, such that the connector piece can be rotated about the horizontal rotation axis;
     a right connector plate, which is connected to an upper part of the rotatable connection, such that the right connector plate protrudes vertically when the rotatable connection is in a non-related position, wherein the right connector plate further comprises a right pivotal aperture;
     a left connector plate, which is connected to an upper part of the rotatable connection, such that the left connector plate protrudes vertically when the rotatable connection is in the non-rotated position, wherein the left connector plate further comprises a left pivotal aperture;
   the right and left connector plates are parallel and mounted side by side, such that there is a plate gap between the right and left connector plates, such that the plate gap is configured to accept the insert piece, such that the insert piece is rotatably connected between the right and left pivotal apertures, such that angle markings are configured to indicate the device inclination angle.

14. The angle-guidance device of claim 13, wherein the rotatable connection is the rotatable cylinder.

15. The angle-guidance device of claim 13, wherein the insert piece includes a protractor piece, which includes the angle markings; and wherein at least one of the right and left connector plates further comprises:
   a protractor cutout,
   which is configured such that the angle markings are visible through the protractor cutout.

16. An angle-guidance device, comprising:
   a) a base; and
   b) a guidance piece, which is rotatably connected to an upper side of the base, the guidance piece comprising:
     an insert piece, rotatably connected to the base with respect to a longitudinal rotation axis; and
     a v-shaped needle guide, which is connected to an upper part of the insert piece, the v-shaped needle guide comprising two plates meeting at an axis located at the upper part of the insert piece to form a v-shaped centered above the insert piece;
   wherein the v-shaped needle guide is configured to be inclined up or down, at a device inclination angle of the v-shaped needle guide relative to the base;

whereby a biopsy needle is adapted to be guided by the v-shaped needle guide, such that the biopsy needle slides in the bottom inside of the v-shaped needle guide, such that the biopsy needle is adapted to be inserted in a patient with a redetermined device inclination angle;

c) a threaded protractor bolt;

d) a protractor nut;

e) a threaded connector bolt;

f) a connector piece, further comprising:
    a front connector flange, with a front flange aperture; and
    a rear connector flange, with a threaded rear flange aperture;

g) a center connector, with a center aperture, such that the center connector is mounted on an upper side of the base;

wherein the front and rear connector flanges are configured to slide on respectively a front and rear of the center connector, such that the center connector is mounted in between the front and rear connector flanges, wherein the threaded connector bolt is insertable through the front flange aperture and the center aperture, such that the threaded connector bolt is configured to be screwed into the threaded rear flange aperture, wherein the connector piece is rotatably connected to the center connector;

wherein the threaded protractor bolt is configured to be insertable through right and left connector plate apertures and a protractor aperture of the insert piece, and wherein the threaded protractor bolt is secured in place with the protractor nut screwed on an end of the treaded protractor bolt.

* * * * *